(12) United States Patent
Landi et al.

(10) Patent No.: US 6,264,618 B1
(45) Date of Patent: Jul. 24, 2001

(54) SAMPLING DEVICE AND METHOD OF RETRIEVING A SAMPLE

(75) Inventors: Michael K. Landi, Kenmore; Douglas Moreland, Buffalo, both of NY (US)

(73) Assignee: Minrad, Inc., Buffalo, NY (US)

( * ) Notice: Subject to any disclaimer, the term of this patent is extended or adjusted under 35 U.S.C. 154(b) by 0 days.

(21) Appl. No.: 09/494,013

(22) Filed: Jan. 28, 2000

Related U.S. Application Data (60) Provisional application No. 60/117,616, filed on Jan. 28, 1999.

(51) Int. Cl.$^7$ .................................................. A61B 10/00
(52) U.S. Cl. ........................ 600/567; 600/564; 606/167
(58) Field of Search .................................. 600/562, 564, 600/567; 606/167, 170, 184, 185

(56) References Cited

U.S. PATENT DOCUMENTS

| | | | |
|---|---|---|---|
| 5,108,404 | * | 4/1992 | Scholten et al. ........................ 606/94 |
| 5,300,035 | * | 4/1994 | Clement ........................... 604/167.01 |
| 5,364,372 | * | 11/1994 | Danks et al. .......................... 604/264 |
| 5,380,288 | * | 1/1995 | Hart et al. ......................... 604/167.04 |
| 5,556,411 | * | 9/1996 | Taoda et al. ........................... 606/185 |
| 5,660,186 | * | 8/1997 | Bachir ................................. 600/562 |
| 5,693,031 | * | 12/1997 | Ryan et al. ....................... 604/167.03 |
| 5,735,867 | * | 4/1998 | Golser et al. .......................... 606/185 |
| 5,810,841 | * | 9/1998 | McNeirney et al. .................. 606/130 |
| 5,911,714 | * | 6/1999 | Wenstrom, Jr. ....................... 604/506 |
| 6,022,324 | * | 2/2000 | Skinner ................................ 600/566 |

\* cited by examiner

*Primary Examiner*—Robert L. Nasser
*Assistant Examiner*—Charles Marmor, II
(74) *Attorney, Agent, or Firm*—Hodgson Russ LLP (57) ABSTRACT

A sampling device and method of retrieving a sample are disclosed. The device includes a cannula having a first end and a second end. The first end has a threaded section. The method includes providing a stylet, providing a cannula having an axial channel, and inserting the stylet into the axial channel. Then, the stylet is connected to the cannula to form an assembly, and the assembly is inserted into a body to place an end of the cannula proximate to a sample location. Next, the stylet is disconnected, and the cannula is twisted to engage an end of the cannula in a part of the body. The stylet is removed from the axial channel, and a core collector is inserted in place of the stylet. Once the core collector is connected to the cannula, the cannula is twisted to further engage the end of the cannula in the part of the body, and to embed a portion of the core collector in the part of the body, so that a sample to be retrieved resides in the core collector. Then, the core collector is disconnected from the cannula, and removed from the cannula.

12 Claims, 7 Drawing Sheets

SAMPLING DEVICE AND METHOD OF RETRIEVING A SAMPLE

CLAIM OF PRIORITY

This application claims the benefit of U.S. Provisional Application No. 60/117,616, filed Jan. 28, 1999, and that Provisional Application is hereby incorporated herein by reference.

BACKGROUND OF THE INVENTION

1. Field of the Invention

This invention relates to sampling devices and methods of retrieving a sample. The device and method disclosed herein may be used to obtain a sample of bone from a patient.

2. Discussion of Related Art

Existing methods of percutaneous bone biopsy involve placement of a needle into the bone using a fluoroscope or cat-scan to guide a physician to properly position the needle. The needle is then moved axially within the bone, slightly changing the angle of the needle with each advancement to provide samples of the bone to the interior channel of the needle. The interior channel of the needle is aspirated to remove body fluids. Normally, the needle must be rocked back and forth to fracture the bone in order to provide the sample. Once the bone sample is obtained, the needle is removed and the bone sample is evaluated.

Frequently, the bone sample is left behind when the needle is withdrawn and no bone is obtained. If an inadequate sample is obtained, or if multiple samples are required, the procedure must be repeated, thereby increasing the cost of the procedure, exposing the patient and medical personnel to harmful x-rays, in the case where a fluoroscope is used to properly position the needle, and exposing the patient to additional risk corresponding to complications from the procedure.

SUMMARY OF THE INVENTION

Accordingly, it is an object of the present invention to provide a device for and method of performing a bone biopsy. The foregoing objective is realized by the present invention, which includes a sampling device and a method of retrieving a sample. The device includes a cannula having a first end and a second end. The first end has a threaded section.

The present invention also includes a method of obtaining a bone sample. The method includes providing a stylet, providing a cannula having an axial channel, and inserting the stylet into the axial channel. Then, the stylet is connected to the cannula to form an assembly, and the assembly is inserted into a body to place an end of the cannula proximate to a sample location. Next, the stylet is disconnected, and the cannula is twisted to engage an end of the cannula in a part of the body. The stylet is removed from the axial channel, and a core collector is inserted in place of the stylet. Once the core collector is connected to the cannula, the cannula is twisted to further engage the end of the cannula in the part of the body, and to embed a portion of the core collector in the part of the body, so that a sample to be retrieved resides in the core collector. Then, the core collector is disconnected from the cannula, and removed from the cannula.

BRIEF DESCRIPTION OF THE DRAWINGS

For a fuller understanding of the nature and objects of the invention, reference should be made to the following detailed description taken in conjunction with the accompanying drawings, in which.

BEST MODE FOR CARRYING OUT THE INVENTION

Figure 1:
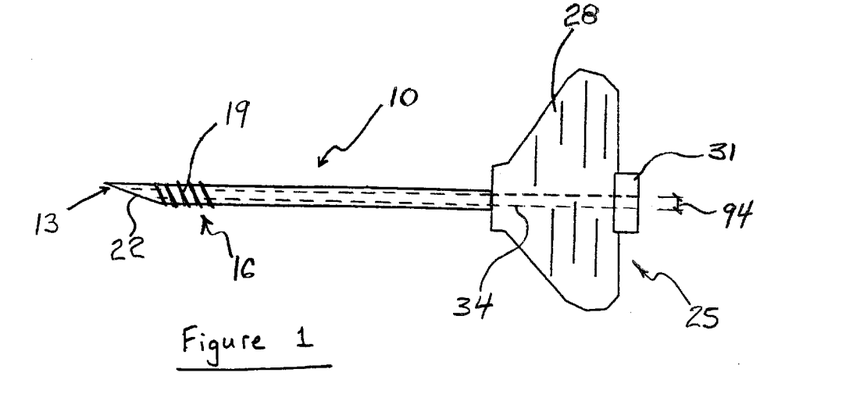
FIG. 1 is a side view of a cannula according to the present invention.

FIG. 1 shows a cannula 10 according to the present invention. The cannula 10 has a first end 13 having a threaded section 16 with a projecting helical rib 19. The first end 13 may include a beveled tip 22, as shown in FIG. 1. The cannula 10 also has a second end 25 having a handle 28. The second end 25 also includes an apparatus for connecting 31 the cannula 10, such as a pin lock connector, that permits the cannula 10 to be connected to another instrument. The cannula 10 has an axial channel 34 extending between the first and second ends 13, 25 of the cannula.

Figure 2:
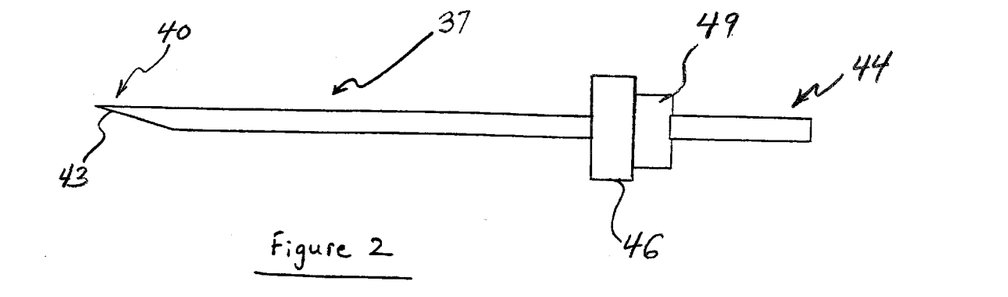
FIG. 2 is a side view of a stylet according to the present invention.

FIG. 2 shows a stylet 37 according to the present invention. The stylet 37 has a first end 40 with a sharpened point 43. The stylet 37 has a second end 44 that may include a device for connecting 46 the stylet, such as a mating apparatus to the pin lock connector. The second end 44 may also include a guidance device 49. Such a guidance device 49 is disclosed more fully in U.S. Pat. No. 5,810,841, and is hereby incorporated by reference. When the stylet 37 is properly aligned with a guidance beam 52, a detectable signal 55 is emitted from the guidance device 49 on the stylet 37. The detectable signal 55 may be a sound or may be visible light.

Figure 3:
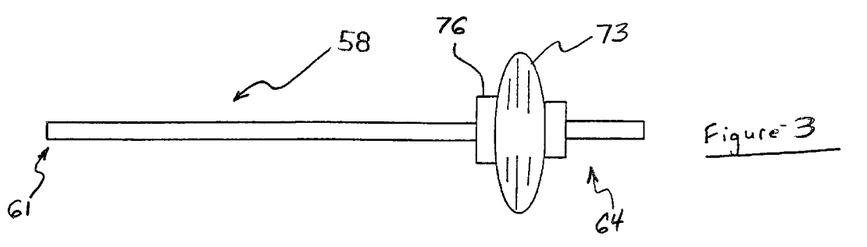
FIG. 3 is a side view of a core collector according to the present invention.
Figure 4:
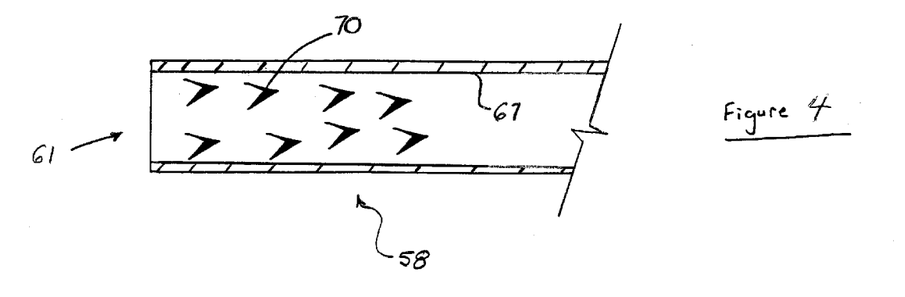
FIG. 4 is a cross-sectioned side view of a portion of the core collector.

FIG. 3 shows a core collector 58 according to the present invention. The core collector 58 has a first end 61 and a second end 64. The core collector 58 has an axial cavity 67 extending between the first and second ends 61, 64 of the core collector 58. FIG. 4 shows a cross-sectioned view of the first end 61 of the core collector 58. Proximate to the first end 61 of the core collector 58 are one or more teeth 70 extending from the core collector 58 into the axial cavity 67.

Figure 5:
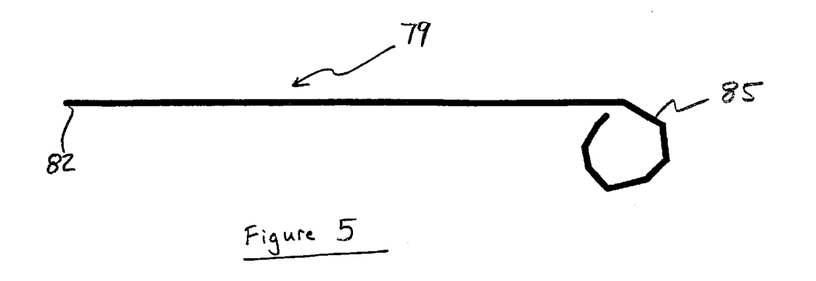
FIG. 5 is a side view of a core ejector according to the present invention.

The second end 64 of the core collector 58 includes a haft 73, and also includes a device for connecting 76 the core collector, which may be similar to the mating apparatus to the pin lock connector, described above. FIG. 5 shows a sample ejector 79 having a blunt end 82 and a handle end 85.

Figure 6:
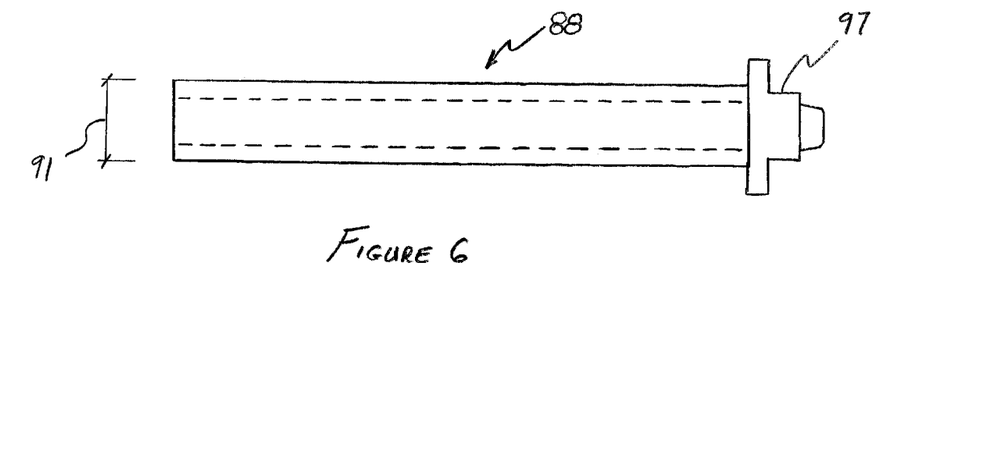
FIG. 6 is a cannula liner according to the present invention.

FIG. 6 shows a cannula liner 88. The cannula liner 88 is a tubular instrument having an outside diameter 91 slightly smaller than the diameter 94 of the axial channel 34 in the cannula 10. The liner 88 may be provided with a fitting 97 for attaching a syringe for injecting filler material, such as bone cement. The fitting 97 may be a conical fitting with a Luer taper, such as that described in ISO 594-2, first edition 1991-05-01, published by the International Organization for Standardization.

Figure 7A:
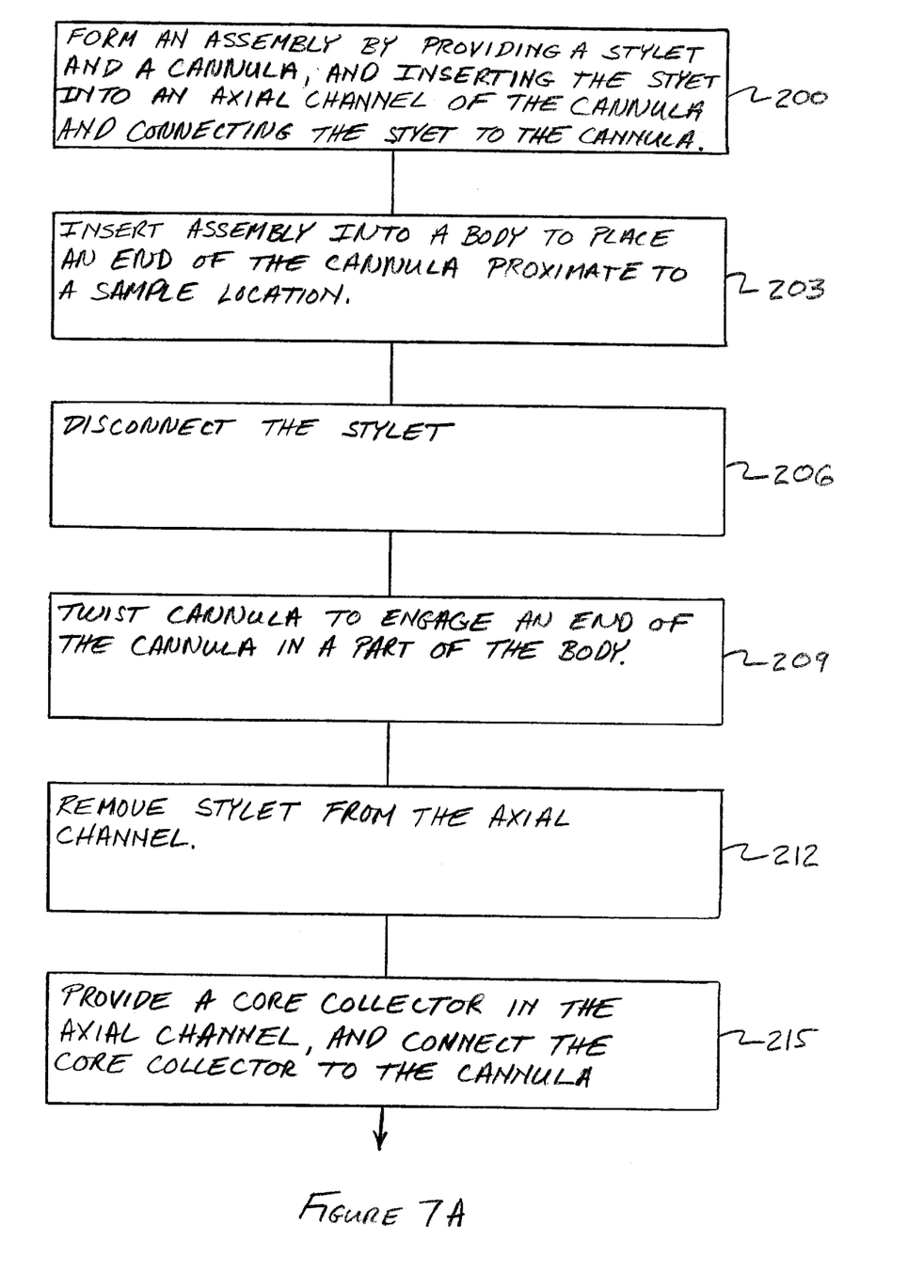
FIGS. 7A and 7B show steps of a method according to the present invention.
Figure 7B:
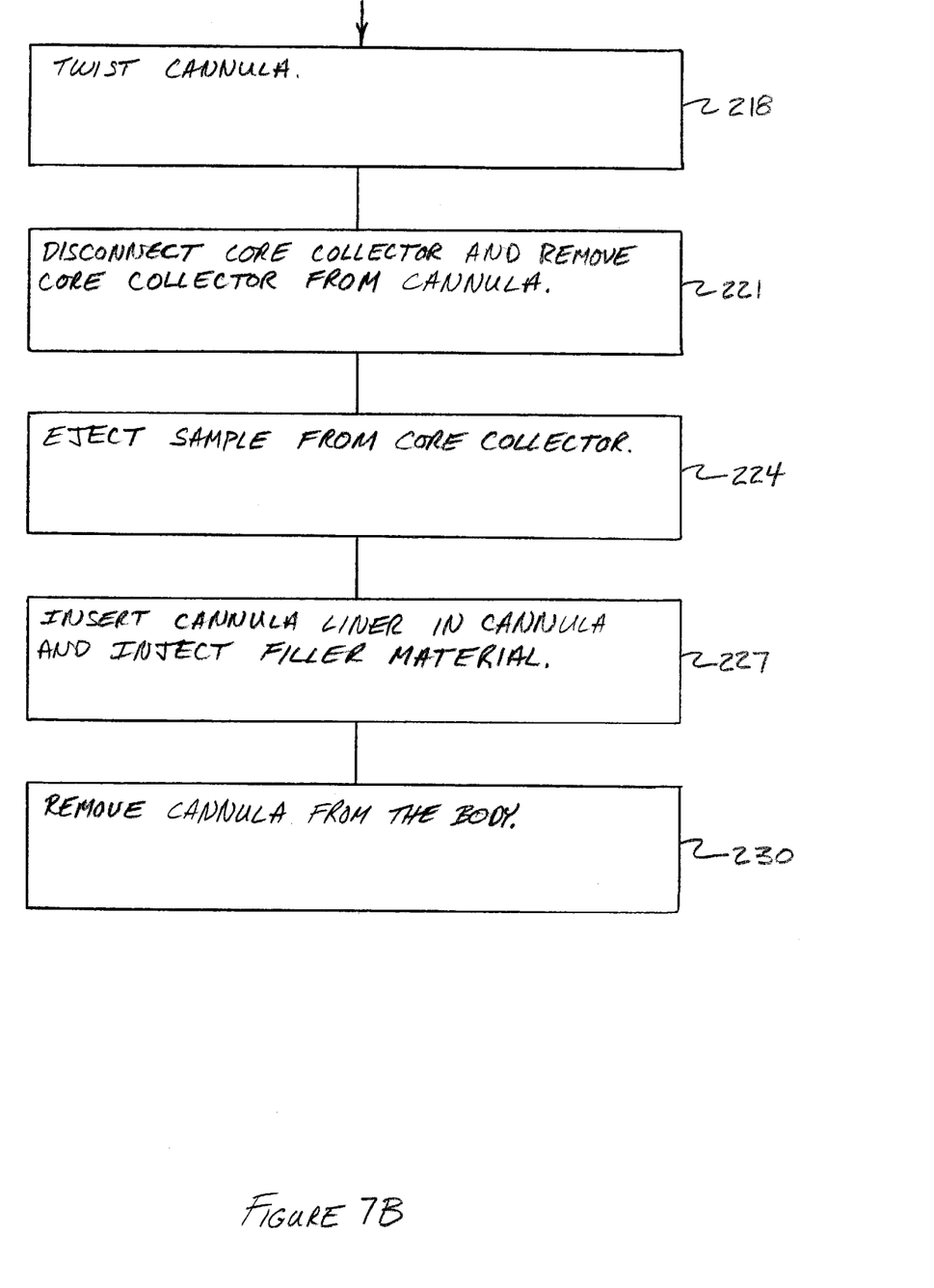

FIGS. 7A and 7B show steps of a method according to the present invention. First, an assembly is formed (step 200) by providing a stylet and a cannula similar to those described above, and inserting the stylet into the axial channel of the cannula so the sharpened point of the stylet is proximate to the first end of the cannula. The stylet may have a guidance device similar to that described above. The sharpened point may extend from the cannula depending on the particular shape of the stylet and the cannula, as well as the particular procedure being performed with the stylet and cannula.

Figure 8:
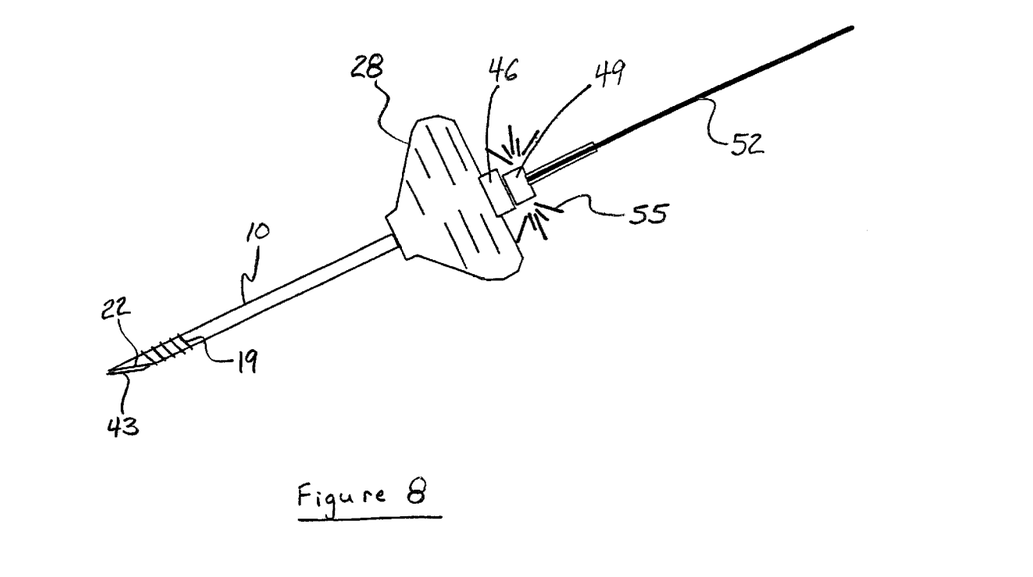
FIG. 8 is a side view of a cannula assembled with a stylet according to the present invention.

The stylet is then connected to the cannula via the apparatus for connecting the cannula mating with the device for connecting the stylet. FIG. 8 shows the stylet inserted in the cannula.

Next, the stylet and cannula assembly is inserted (step 203) into the patient until the first end of the cannula is proximate to the bone to be sampled. The stylet cuts soft tissue surrounding the bone to be sampled, and guides the cannula through the soft tissue in order to place the first end of the cannula proximate to the bone at a sample location where the sample is to be taken. When the stylet includes the guidance device, the stylet is inserted at an angle and at a location signified by a guidance beam.

Figure 9:
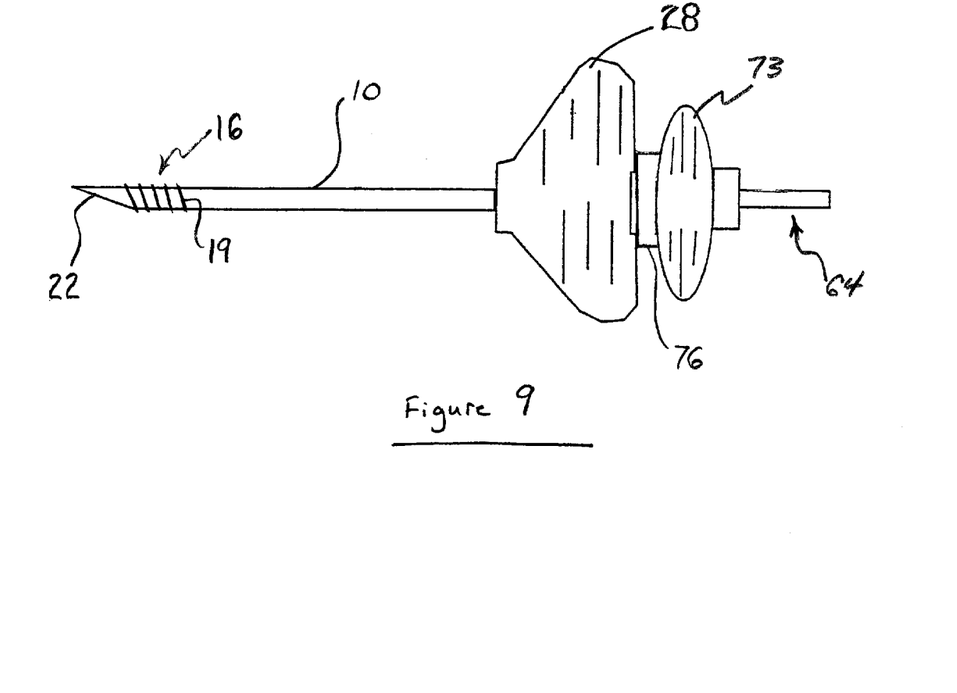
FIG. 9 is a side view of the core collector shown in FIG. 3 assembled with the cannula shown in FIG. 1.

Once the first end of the cannula is proximate to the sample location, the stylet is disconnected (step 206) from the cannula and the cannula is twisted (step 209) via the handle so the helical rib engages the bone, and part of the threaded section is screwed into the bone. Next, the stylet is removed (step 212) from the cannula. In its place, the core collector is provided and inserted (step 215) into the channel of the cannula so the first end of the core collector is proximate to the bone. FIG. 9 shows the core collector inserted in the cannula. The apparatus for connecting the cannula is connected to the device for connecting the core collector. Then the cannula is again twisted (step 218) via the handle to further screw the threaded section of the cannula into the bone and to embed the core collector into the bone.

Next, the core collector is disconnected from the cannula and pulled out of the bone (step 221) via the haft. As the core collector is pulled, the teeth of the core collector engage the bone specimen residing in the axial cavity of the core collector, and prevent the bone specimen from being left in the patient. The core collector, with the bone specimen therein, is removed from the cannula by further pulling on the haft.

Figure 10:
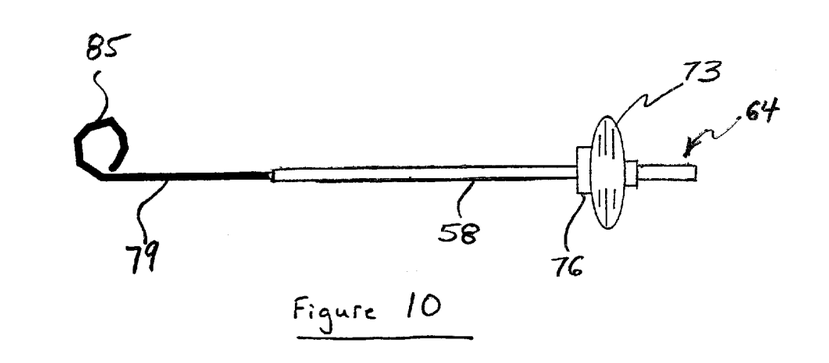
FIG. 10 is a side view of the core ejector shown in FIG. 5 being used to push a bone sample from the core collector shown in FIG. 3.

The blunt end of the sample ejector is then inserted into the axial cavity of the core collector, as shown in FIG. 10. By pushing on the handle end of the sample ejector, the blunt end is forced from the first end of the core collector toward the second end of the core collector in order to eject (step 224) the bone sample from the core collector.

Next, a cannula liner may be inserted (step 227) into the cannula, and bone cement may be injected through the liner to fill the section of bone where the bone sample was removed. The liner prevents the bone cement from contacting the cannula and hardening on the cannula. If the bone cement hardens in the liner, the liner can be removed and replaced with another liner without disturbing the cannula. Finally, the cannula is removed (step 230) from the patient.

Figure 11:
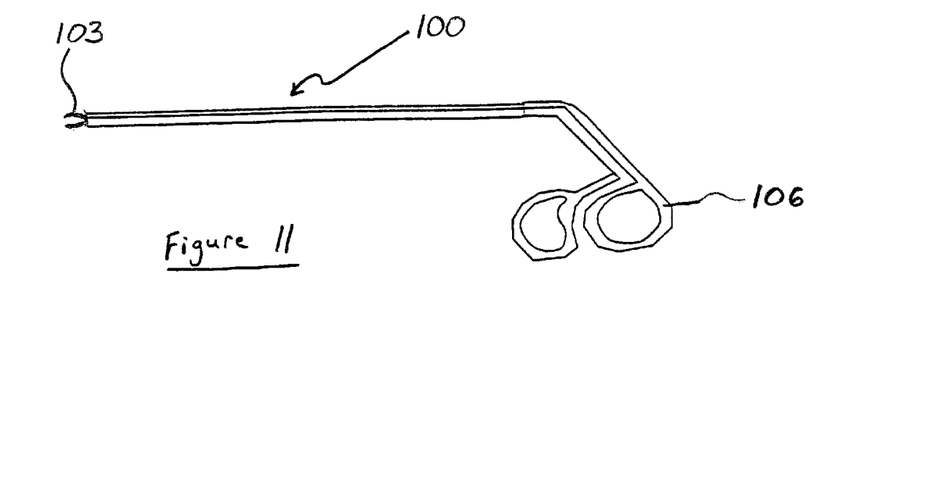
FIG. 11 shows pituitary forceps used in a method according to the present invention.
Figure 12:
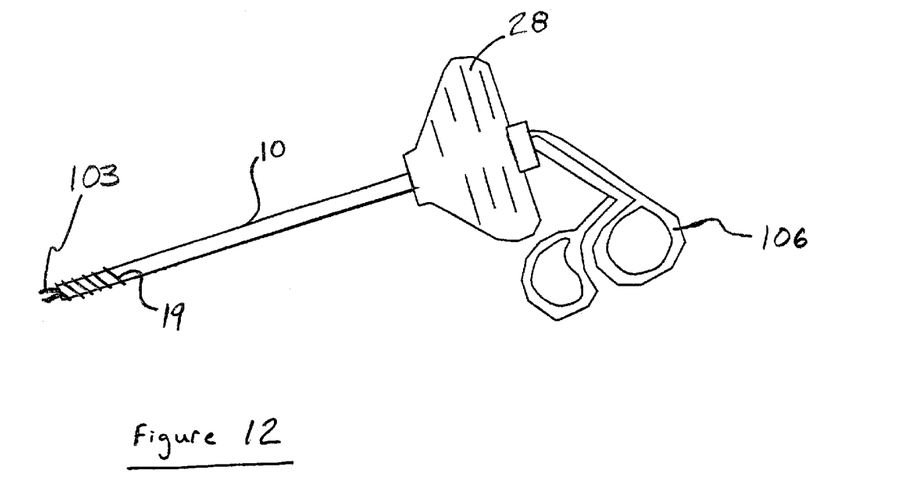
FIG. 12 shows the pituitary forceps shown in FIG. 11 inserted through the cannula shown in FIG. 1.

In another method according to the present invention, pituitary forceps 100 shown in FIG. 11 are used in lieu of the core collector 58. Once at least part of the threaded section 16 is screwed into the bone as described above in step 209, the cannula 10 is unscrewed from the bone and the first end 13 is left proximate to the bone. Pituitary forceps 100 are inserted through the axial channel 34 of the cannula 10 so the jaws 103 of the pituitary forceps 100 are proximate to the bone. Next, the forceps 100 are manipulated by moving the finger rings 106 relative to each other until the bone sample is grasped by the jaws 103. FIG. 12 shows the pituitary forceps 100 inserted in the cannula 10. The pituitary forceps 100 are then removed from the cannula 10, with the bone sample in the jaws 103. The method then continues as described above by inserting the cannula liner 88 and filing the bone with bone cement.

The instruments described above can also be used for other procedures, such as cementoplasty of bones or a venogram. With regard to the cementoplasty and venogram procedures, it should be noted the core collector 58 is not used. With regard to the syringes mentioned above, it should be noted that bone cement has a relatively rapid polymerization time and high viscosity. Therefore, in performing a method according to the present invention, it is preferable to inject bone cement using syringes having a small capacity, for example, a capacity of from 1 to 3 cubic centimeters.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A sampling device, comprising:
    a cannula having a first end and a second end, wherein the first end has a threaded section on an outer surface of the cannula, and having an axial channel therethrough extending between the first and second ends;
    a cannula liner disposed within the axial channel, the liner having an orifice therethrough; and
    cement disposed in the liner.

2. The device of claim 1, wherein the threaded section includes a projecting helical rib.

3. The device of claim 1, wherein the first end includes a beveled tip.

4. The device of claim 1, wherein the second end has a handle.

5. The device of claim 1, wherein the second end includes an apparatus for connecting the cannula to an instrument.

6. The sampling device of claim 1, wherein the cement is bone cement.

7. The device of claim 1, wherein the cannula liner is tubular.

8. The device of claim 1, wherein the cannula liner includes a conical fitting having a Luer taper.

9. A method of retrieving a sample, comprising:
    providing a stylet;
    providing a cannula having an axial channel;
    inserting the stylet into the axial channel;
    connecting the stylet to the cannula to form an assembly;
    inserting the assembly into a body to place an end of the cannula proximate to a sample location;

disconnecting the stylet;

twisting the cannula to engage an end of the cannula in a part of the body;

removing the stylet from the axial channel;

providing a core collector;

inserting the core collector into the axial channel;

connecting the core collector to the cannula;

twisting the cannula to further engage the end of the cannula in the part of the body and to embed a portion of the core collector in the part of the body, and so that a sample to be retrieved resides in the core collector;

disconnecting the core collector from the cannula;

removing the core collector from the axial channel;

providing a sample ejector;

contacting the sample with the sample ejector to force the sample from the core collector;

providing a cannula liner in the axial channel; and causing filler material to flow through the liner to a location previously occupied by the sample.

10. A method of retrieving a sample, comprising:

providing a cannula having an axial channel and a threaded section;

twisting the cannula to engage the threaded section in a body at a sample location;

removing a sample of the body from the sample location through the axial channel;

providing a cannula liner in the axial channel; and causing filler material to flow through the liner to the sample location.

11. The method of claim 10, further comprising:

providing a core collector;

inserting the core collector into the axial channel; and embedding a portion of the core collector in the body at the sample location.

12. The method of claim 11, further comprising:

removing the core collector from the axial channel;

providing a sample ejector; and contacting the sample with the sample ejector to force the sample from the core collector.

\* \* \* \* \*